(12) United States Patent
McGrath et al.

(10) Patent No.: US 9,459,326 B2
(45) Date of Patent: Oct. 4, 2016

(54) BATTERY PACK AND ELECTRICAL DEVICE WITH DEMOUNTABLE BATTERY PACK

(75) Inventors: Matthew John Ross McGrath, Edinburgh (GB); Peter Douglas Colin Inglis, Edinburgh (GB); Brian Alan Laffoley, Edinburgh (GB)

(73) Assignee: Covidien LP, Mansfield, MA (US)

( * ) Notice: Subject to any disclaimer, the term of this patent is extended or adjusted under 35 U.S.C. 154(b) by 716 days.

(21) Appl. No.: 13/697,625

(22) PCT Filed: May 13, 2011

(86) PCT No.: PCT/GB2011/050925
§ 371 (c)(1),
(2), (4) Date: Nov. 13, 2012

(87) PCT Pub. No.: WO2011/141752
PCT Pub. Date: Nov. 17, 2011

(65) Prior Publication Data
US 2013/0072757 A1  Mar. 21, 2013

(30) Foreign Application Priority Data

May 13, 2010 (GB) .................................. 1008020.8
Oct. 13, 2010 (GB) .................................. 1017292.2

(51) Int. Cl.
*A61B 1/267* (2006.01)
*G01R 31/36* (2006.01)
(Continued)

(52) U.S. Cl.
CPC ....... *G01R 31/3648* (2013.01); *A61B 1/00034* (2013.01); *A61B 1/04* (2013.01);
(Continued)

(58) Field of Classification Search
CPC ..... A61B 1/267; A61B 1/24; A61B 1/00032
USPC .................................................. 600/184–200
See application file for complete search history.

(56) References Cited

U.S. PATENT DOCUMENTS 5,178,131 A   1/1993  Upsher
5,707,757 A   1/1998  Lee
(Continued)

FOREIGN PATENT DOCUMENTS

WO         9806144      2/1998
WO      WO 98/06144     2/1998

OTHER PUBLICATIONS

International Search Report for PCT/GB2011/050922, mailed Aug. 4, 2011, 7 pages.
(Continued)

*Primary Examiner* — Ellen C Hammond
*Assistant Examiner* — Christina Negrellirodrigue
(74) *Attorney, Agent, or Firm* — Fletcher Yoder PC

(57) ABSTRACT

A battery pack (10) for an electrical device (60) has a cover portion which forms part of the assembled electrical device (60) and a seal (78) for forming a waterproof seal between the battery pack (10) and the electrical device (10). Thus, every new battery pack can form a fresh seal with the electrical device (60), allowing effective waterproofing. A battery pack (10) for an electrical device (60) includes a memory storing a value indicative the remaining available rated capacity of the battery pack (10). The stored value is changed in use to reflect reducing capacity. The initial stored value is chosen so that there is a very high (e.g. >99.9%) confidence that the battery pack will provide at least the capacity indicated by the initial stored value. This reduces the chance of failure during emergency procedures. An override facility is provided. A laryngoscope (60) comprising a handle comprising a demountable battery pack (10) comprising one or more batteries (20) and an arm (49) operable to retain a demountable laryngoscope blade.

20 Claims, 12 Drawing Sheets

(51) Int. Cl.
  *H01M 2/08* (2006.01)
  *H01M 2/10* (2006.01)
  *H01M 6/50* (2006.01)
  *H01M 10/48* (2006.01)
  *A61B 1/04* (2006.01)
  *A61B 1/00* (2006.01)

(52) U.S. Cl.
  CPC .......... *A61B 1/267* (2013.01); *G01R 31/3606* (2013.01); *H01M 2/08* (2013.01); *H01M 2/1066* (2013.01); *H01M 2/1094* (2013.01); *H01M 6/50* (2013.01); *H01M 10/48* (2013.01); *H01M 10/488* (2013.01); *A61B 1/00029* (2013.01); *H01M 6/5044* (2013.01)

(56) References Cited

U.S. PATENT DOCUMENTS

| | | | |
|---|---|---|---|
| 7,946,981 B1* | 5/2011 | Cubb | A61B 1/00052 600/120 |
| 2003/0088156 A1* | 5/2003 | Berci | A61B 1/00188 600/188 |
| 2007/0179342 A1* | 8/2007 | Miller | A61B 1/267 600/188 |
| 2008/0182164 A1 | 7/2008 | Lu et al. | |

OTHER PUBLICATIONS

Written Opinion for PCT/GB2011/050922, mailed Aug. 4, 2011, 14 pages.

* cited by examiner

BATTERY PACK AND ELECTRICAL DEVICE WITH DEMOUNTABLE BATTERY PACK

This application is the U.S. national phase of International Application No. PCT/GB2011/050925 filed 13 May 2011 which designated the U.S. and claims priority to GB Patent Application Nos. 1008020.8 filed 13 May 2010 and 1017292.2 filed Oct. 13, 2010, the entire contents of each of which are hereby incorporated by reference.

FIELD OF THE INVENTION

The invention relates to electrical devices, including electrical medical devices, which are powered by removable batteries and which are operated in environments where they may come into contact with liquid.

BACKGROUND TO THE INVENTION

Electrical devices, such as electrical medical devices, may incorporate a battery power supply to enable them to be used without the limitations of a power cable.

Many such electrical devices may be used in environments where they may come into contact with liquid. For example, electrical medical device for in vivo use may be used in environments where they come into contact with bodily fluids and electrical medical devices which include reusable portions requiring decontamination between uses may be used in environments where they come into contact with cleaning products.

It is often necessary for such electrical devices to be sealed against penetration by liquid to prevent damage to the device or loss of battery power.

A secondary concern is to avoid gaps leading to spaces where microbes can proliferate, and which can be prove difficult to clean.

Many known electrical devices powered by removable batteries comprise a battery compartment, having a cover, into which one or more removable batteries may be mounted. When inserting or removing batteries from the battery compartment it is necessary to remove and/or reattach the cover. Therefore, it is difficult to maintain a high quality seal between the cover and the remainder of the electrical device. In addition, the quality of the seal may deteriorate further each time that the seal is broken.

It is known to provide electrical devices containing rechargeable batteries which remain sealed within the device. However, the maximum capacity (in usable ampere hours) of the rechargeable batteries decreases with repetitive use. Furthermore, it is not possible to carry out some decontamination procedure (e.g. autoclaving, irradiation) on electrical device from which batteries cannot be removed.

Thus, the aim of some aspects of the invention is to provide an electrical device (for example, an electrical medical device such as a laryngoscope) which is reliably sealed against penetration by liquid and from which one or more batteries can be removed and replaced, and the seal reformed reliably without specialist sealing procedures being required.

Another known problem with battery powered electrical devices, including electrical medical devices such as laryngoscopes, is that the batteries may be depleted and the power supply may fail during use. The battery compartments of such devices will typically receive any of a wide range of batteries having a similar external shape but substantially different electrical properties and capacities. Furthermore, it may not be apparent if a battery has been used before. Thus, it may not be possible to predict exactly when the power supply may fail. Thus, in many known devices, there is a substantial risk of a failure in the power supply during use. This is of particular concern in relation to electrical medical devices, such as laryngoscopes, which may be used in emergency procedures. This risk of a failure in the power supply can be reduced by using new batteries for each procedure. However, this is very wasteful.

Accordingly, some aspects of the invention aim to provide improved methods of minimising the risk of the battery power supply of an electrical device failing during a procedure.

SUMMARY OF THE INVENTION

According to a first aspect of the invention there is provided an electrical device comprising a body and a battery pack demountably attachable to the body, the body of the electrical device comprising at least one input interface for receiving power from a demountable battery pack, the demountable battery pack comprising a cover portion, a seal, a battery, and an output interface for transmitting electrical power, whereby when the battery pack is demountably attachable to the body such that (in the resulting assembled device with the battery pack demountably attached to the body) the input and output interfaces are in electrical communication, the cover portion of the battery pack forms part of the outer surface of the assembled device, and the seal forms a waterproof seal between the demountable battery pack and the body of the electrical device.

Thus, by providing a seal as part of the demountable battery pack, a reliable seal can be formed each time that a new battery pack is fitted, as each new battery pack will include a new seal.

The battery pack is preferably intended for a limited period of use and disposal or return to a facility provided manufacturer for refurbishment. The battery pack is preferably not rechargeable by the end user. The seal may be a single-use seal.

As the battery pack includes a cover portion which forms part of the exterior of the assembled device, the seal need only form a new sealing contact with the body of the medical device. It does not need to form new sealing contacts with both the body of the medical device and a cover, as would be the case for a battery compartment including a reusable cover and a washer or similar seal.

As the battery pack includes a cover portion, the battery pack can fit into a recess in the electronic device and the resulting electronic device may be more compact than would be the case if the device had a separate cover.

Thus body and battery pack are configured such that the cover portion of the battery pack and an outer surface of the assembled device fit together, when the battery pack is demountably attachable to the body, with the waterproof seal therebetween, such that the cover portion of the battery pack can form part of the outer surface of the assembled device while the input and output interfaces are in electrical communication.

Preferably, the battery pack has a coupling surface extending around the battery pack, and the body of the electrical device comprises a cooperating surface such that, when the battery pack is mounted to the body of the electrical device, the coupling surface and cooperating surface fit against each other, with the seal therebetween. Typically, the seal extends around the coupling surface. The seal may extend around the cover portion thereby forming a seal at the outer surface of the assembled device, minimising cracks which may retain contaminants, moisture etc. The seal may be compressed between the battery pack and the body of the medical device, for example, between the said coupling surface and cooperating surface of the body of the electrical device, when the battery pack is mounted to the body of the electrical device.

The body of the electrical device may comprise a recess for receiving the demountable battery pack. The cover portion may occlude the recess when the device is assembled. Prior to mounting, the seal may have a slightly greater extent than the recess.

The seal is typically compliant and may, for example, be plastically deformable. The seal may comprise a ridge. The seal may comprise a washer, such as an O ring, mounted within a corresponding recess of the disposable battery pack. The seal may comprise a single use adhesive.

The seal may comprise flexible hydrophobic polymeric material to repel water from the seal join. The seal may comprise a hydrophobic coating formed around the demountable battery pack. The seal may comprise a hydrophilic or hydrophobic coating.

A seal may comprise a plurality of seal portions. The battery pack may comprise a plurality of seals. The demountable battery pack may have at least a first seal and a second seal. The first and second seals may be concentric. The first and second seals may be configured such that each forms a seal intermediate the outside of the medical device and the input and output interfaces, such that liquids outside the device would require to pass both seals in turn to penetrate the inputs and output interfaces. The first seal may be located closer to the cover portion than the second seal. For example, the first seal and the second seal may each extend around the said coupling surface, with the first seal closer to (e.g. at) the surface of the cover portion which forms part of the outer surface of the assembled device in use. The first and second seals may have different compositions, to resist different types of material, for example, one seal may resist aqueous solvents. The other may resist specific non-aqueous solvents.

The cover portion of the battery pack may comprise a locking formation operable to lock the battery pack tightly to the body of the electrical device. In embodiments where the body of the electrical device comprises a recess, the body of the electrical device may comprise locking mechanism operable to cooperatively receive the locking formation on the battery pack. The locking mechanism may allow the user of the electrical device to apply force on to the seals of the battery pack and thereby form an effective seal between the cooperating surface of the electrical device body and the coupling surface of the battery pack.

The surface of the body of the electrical device opposed to the said recess may comprise a cooperative feature mechanically connected to the locking mechanism, wherein the user twists a cooperating feature (e.g. inserts a portion of a coin into the cooperating feature) and turns the cooperating formation to lock or unlock the battery pack in position on the body of the electrical device.

For example, the locking mechanism may comprise a cam bolt. The cam bolt may extend through the body of the electrical device and cooperatively receive the locking formation on the battery pack. Rotation of the cam bolt may draw the locking formation into the cam bolt such that the battery pack is urged into the recess.

The battery within the demountable battery pack or the demountable battery pack itself may be fully sealed such that the battery or battery pack, and typically also the electronic device with battery or battery pack is submersible, that is to say, is not damaged by temporary submersion in water. Preferably, the electrical device with fitted battery pack is fully submersible (can be temporarily submerged in water without damage). The battery or the battery pack may comprise an isolator to selectively isolate one terminal of the battery, or battery pack, respectively. For example, the battery or battery pack may comprise a reed-relay that is open by default and is activated by a magnet in the body of the electrical device such that when the battery or battery pack is mounted onto the body of the electrical device, the reed-relay is activated by the magnet and the battery or battery pack then becomes "live".

In the unlikely event that a seal fails during a decontamination procedure, the electrical current between the two terminals of the battery may create a potential difference between themselves such that electrolysis of the decontamination fluid occurs. Accordingly, such electrolysis reduces the residual charge of the battery and would typically produce a build up of deposited material (content dependent upon the solution that is surrounding the battery) on one of the terminals.

Therefore, providing a battery within the demountable battery pack which may be fully sealed or the provision of a battery terminal within the demountable battery pack which may be disconnected prevents unwanted discharge of the battery or batteries and potential degradation of the terminals of the battery or batteries within the demountable battery pack in the event of a seal failure during decontamination.

Where an electrical device comprises a handle, the cover of the battery pack may form a portion of the handle of the electrical device. The battery pack cover may comprise an anti-slip surface to facilitate grip. The anti-slip surface may comprise a textured surface.

The battery pack comprises a switch operable to activate the electrical device. Thus, in typical embodiments powered only by one battery pack, the electrical device cannot be activated when a battery pack is not mounted to the body of the device. Typically the switch is located on the battery pack cover.

The cover of the battery pack (e.g. the switch) may comprise a display to inform the user whether the electrical device is activated or whether the electrical device is deactivated. The display may be a light source, such as an LED. The light source may emit light when the electrical device is activated. The light source may change colour when the device is activated. The display may comprise a plurality of light sources. The display may be operable to display a character or characters to the user.

Preferably, the battery pack comprises a release mechanism to detach the battery pack from the body of the electrical device. The release mechanism may comprise a release formation associated with the perimeter of the battery pack. The release formation may allow a user to lever the battery pack from the body. The release formation may be a tab extending from the battery pack cover. The provision of a release tab for detaching the battery pack reduces the number of mechanical parts within the battery pack, reducing the manufacturing costs and increasing the reliability of the battery pack. The provision of a release tab enables a seal forming a strong bond, which would otherwise be difficult to break, to be employed.

The battery pack comprises one or more batteries. The battery pack typically comprises a battery retaining formation, such as a clip or chamber for retaining one or more batteries. One or more batteries may be permanently mounted to the battery retaining formation. Alternatively, the battery retaining formation may demountably retain one or more batteries.

The battery pack may comprise a memory storing a value indicative of the remaining available rated capacity of the one or more batteries and the electrical device may comprise a usage recording device (such as an electrical circuit, which may be a processor of the electrical device) operable to determine when the electrical device is operated and to update the value stored in the memory responsive to such usage to reflect the consumption of power from the one or more batteries resulting from the said operation.

The invention extends in a second aspect to an electrical device comprising an electrical device body and a battery pack comprising one or more batteries and a memory storing a value indicative of the remaining available rated capacity of the one or more batteries, the electrical device comprising a usage recording device operable to determine when the electrical device is operated and to update the value stored in the memory responsive to such usage to reflect the consumption of power from the one or more batteries resulting from the said operation.

The stored value is therefore the remaining available rated capacity value initially stored in the memory, updated by the actions of the usage recording device. After sufficient use the stored value will be indicative that the initial rated capacity of the one or more batteries has been consumed, for example, the stored value may be progressively reduced until it reaches a value, such as zero, indicative that the available rated capacity has been consumed.

By the rated capacity we refer to the amount of power which can be obtained from the one or more batteries, while the batteries have electrical properties (such as potential difference) sufficient to power normal operation of the electrical device, according to a predetermined (rated) specification of the amount of power which the one or more batteries should provide in a very high proportion of cases. The remaining available rated capacity is the amount of that rated capacity which has not yet been consumed as updated by the usage recording device during use.

The value of remaining available rated capacity initially stored in the memory is selected so that, in a very high proportion of cases, typically at least 99% and preferably at least 99.9% or at least 99.99% of cases, the battery pack will have remaining stored power which could be used to power normal operation of the electrical device when the stored value reaches a value indicative that the rated capacity has been exhausted. Thus, if the battery pack comprises one or more batteries which in aggregate are found to deliver 105.0 to 175.0 mAh in 99.9% of cases, taking into account the range of uses to which the electrical devices are put, the value initially stored in the memory well be set so that it is updated to a value indicative that the initial capacity has been consumed when at most 105.0 mAh have been used.

As a result of this margin for error, if the stored value is indicative that an amount of capacity exceeding that required for a procedure remains stored in the battery pack, the user can have a very high confidence that the electrical device will continue to operate throughout the procedure, reducing the risk of failure which could otherwise occur in devices which enable a user to use any battery of a specific class which encompasses batteries having very different capacities (e.g. AA or AAA batteries, which have compositions and capacities which vary widely between brands and types, for example Alkaline, NiMH or Lithium).

The use of stored values which are updated when use occurs can provide a more accurate estimate of guaranteed remaining capacity than the use of measurements of remaining battery capacity, which can be unreliable, especially when the battery capacity is close to exhausted.

The usage recording device typically determines when use is occurring and transmits signals to the battery pack indicative that the value stored in the memory should be updated. The signals may represent an updated value to be written to the memory, or that the stored value should be changed by a certain amount, for example, incremented or decremented. The usage determining module may communicate wirelessly with the battery pack. For example, the memory may be part of an RFID tag located in the battery pack, read from and written to by a solenoid aerial in the body of the electrical device.

The battery pack may be demountably attachable to the body. Thus, the battery pack may be a battery pack according to the first aspect of the invention.

Preferably, the one or more batteries of the battery pack are disposable batteries. That is, the one or more batteries of the battery pack may not be recharged after the available rated capacity of the one or more batteries has been consumed.

Therefore the battery pack must be replaced when the available rated capacity of the one or more batteries of the battery pack has been consumed.

During the lifetime of rechargeable batteries, the maximum available rated capacity degrades as the battery is repeatably recharged. In addition, the characteristics of the rate of change of the available rated capacity as the battery is used may be changed or degraded, resulting in inaccurate values of available rated capacity. Such inaccuracies could lead to failure of the device during use.

Accordingly, the use of disposable batteries ensures that the stored value of available rated capacity is accurate and dependable such that device failures during use, due to the batteries become depleted, are effectively eradicated.

The battery pack may lack a recharge interface. For example, the battery pack may lack an external power input.

Preferably, the memory is a passive device such that power is only consumed by the memory when data is read from or written to the memory. Thus, where the memory is part of an RFID tag, the RFID tag is preferably a passive RFID tag.

The stored value may be a numerical value representing remaining available rated capacity. The stored value for a new fully charged battery pack may have a predetermined integer value, such as 100, 256, 500 etc. which is progressively decremented by the memory updating module in use, and a battery which has output its rated amount of power would have a stored value of zero. The stored value may count up. The value may be stored in any form, for example, the memory may comprise a plurality of fuses or antifuses which are triggered in turn with the number of fuses or antifuses which have been triggered or which remain untriggered indicating the stored value.

The stored value may be indicative of a number of units of time, such as hours or minutes, of operating of the electrical device (optionally, in one or more modes) for which the battery pack has remaining available rated capacity for a given power consumption. This is especially helpful where the power consumption of the medical device is substantially constant in use. The stored value may be indicative of a number of procedures which the electrical device can carry out using the remaining available capacity (for example, intubation procedures where the electrical device is a video laryngoscope).

The electrical device may display an indicator of the amount of capacity remaining in the battery pack based on the stored value. The indicator may comprise a light source or a plurality of light sources. The plurality of light sources may comprise light sources which emit light of a different colour to each other. The electrical device may comprise a screen and the screen may display the indicator. For example, where the electrical device is a video laryngoscope having a screen, the screen may display the indicator. The indicator may be a number. The indicator may be a number representative of an amount of time, or a number of procedures which the electrical device can carry out using the remaining available capacity (for example, intubation procedures where the electrical device is a video laryngoscope).

The electrical device may comprise a loudspeaker and generate a sound indicative that the remaining capacity determined from the stored value is approaching zero.

The electrical device may stop, or not start, carrying out one or more operating functions once the remaining available rated capacity indicated by the stored value is below a threshold (for example, a few percent of maximum capacity, or zero, or a predetermined negative value). The electrical device may indicate one or more warning to a user before this occurs.

The electrical device may comprise an override to enable a user to continue to carry out, or to start, some or all of the operating functions even though this has occurred. The override may comprise a switch. The override may comprise a loudspeaker and allow a user to continue to carry out, or to start, some or all of the operating functions responsive to a sufficiently loud sound detected by the loudspeaker (e.g. the user shouting at the device from close range). This is advantageous as it allows a user to obtain additional function where required, but it dissuades a user (who would typically not wish to shout in certain environments) from using an override activated by a sufficiently loud sound. The override mechanism may comprise a switch, or another form of user input such as pressure sensors or sound sensors, for example.

Optional features discussed above in relation to either the first or second aspects of the invention are optional features of both the first and second aspect of the invention where context permits.

Typically, an electrical device of the first or second aspect of the invention is an electrical medical device. The medical device may be a handheld medical device, such as an ultrasound scanner, infusion pump controller and infusion pump, diagnostic device, blood monitor, e.g. blood glucose monitor, endoscopes or other devices for probing within the human body.

The electrical device of the first or second aspect of the invention may be an intubation instrument such as a laryngoscope, preferably a video laryngoscope.

In embodiments where the electrical device is a laryngoscope, the laryngoscope may comprise a handle and an arm. The handle may comprise a first end adjacent to the arm, and an opposed second end. The battery pack may be mounted onto the handle of the laryngoscope adjacent to the first end. The battery pack may be mounted equidistant between the first and second end and the one or more batteries within the battery pack may be located adjacent to the first end of the handle.

Preferably, the one or more batteries are located closer to the first end than the second end. Preferably, the centre of mass of the one or more batteries is located at least two-thirds, preferably three-quarters, of the way from the second end to the first end.

The majority of the electronics within the handle of the laryngoscope may be located closer to the first end than the second end, for example, at least two-thirds (or preferably three-quarters) of the way from the second end to the first end. They may be adjacent to the first end of the handle.

In embodiments where the electrical device is a laryngoscope and the laryngoscope body comprises a handle, the provision of a battery and/or the majority of the electronics located closer to the first end of the handle ensures that the centre of gravity of the handle is closer to the first end of the handle than the second end, and ensures that the laryngoscope handle is stabilised within the hand of a user. In addition, the provision of the battery and/or the majority of the electronics being located adjacent to the first end of the electrical device body ensures that the electronics are compact.

The second end of the electrical device body may comprise a low density portion. The low density portion may comprise an air pocket. The low density portion may comprise a low density foam.

Alternatively, the low density portion may comprise a recess in the surface of the electrical device body. The recess may allow the user to grip the electrical device more securely.

Where the electrical device is a video laryngoscope, the laryngoscope may comprise a screen connected to the battery and electronics of the laryngoscope by a connector. The connector may be a physical wire. The connector may be an optical connection such as an optical fibre. The connector may be a wireless connector.

According to a third aspect of the present invention there is provided a kit comprising an electrical device body and a demountable battery pack which together form an electrical device according to the first or second aspect of the present invention.

DESCRIPTION OF THE DRAWINGS

An example embodiment of the present invention will now be illustrated with reference to the following Figures in which.

DETAILED DESCRIPTION OF EXAMPLE EMBODIMENTS

First Embodiment

Figure 1:
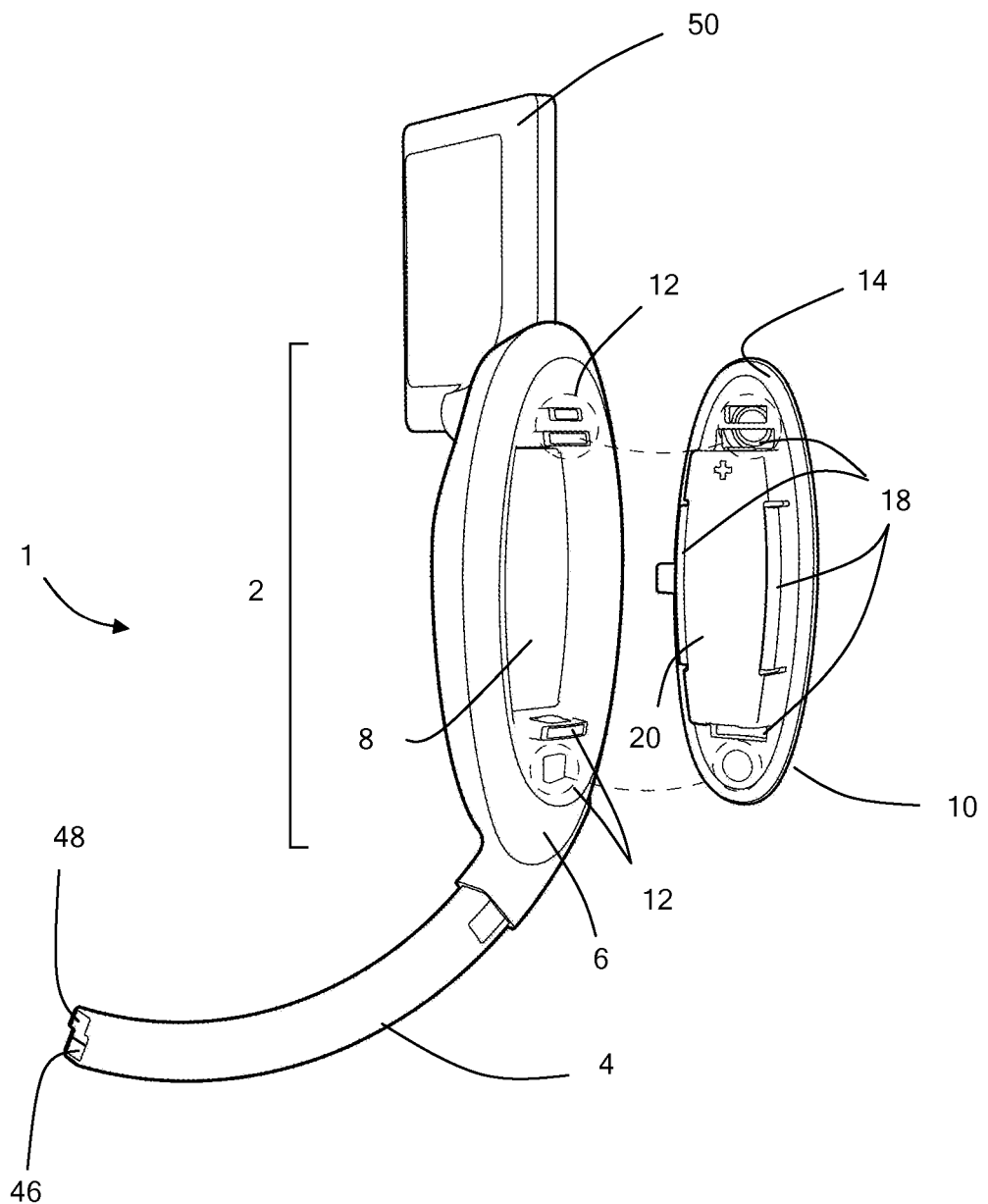
FIG. 1 is an exploded isometric view of a video laryngoscope with the battery pack removed.
Figure 2:
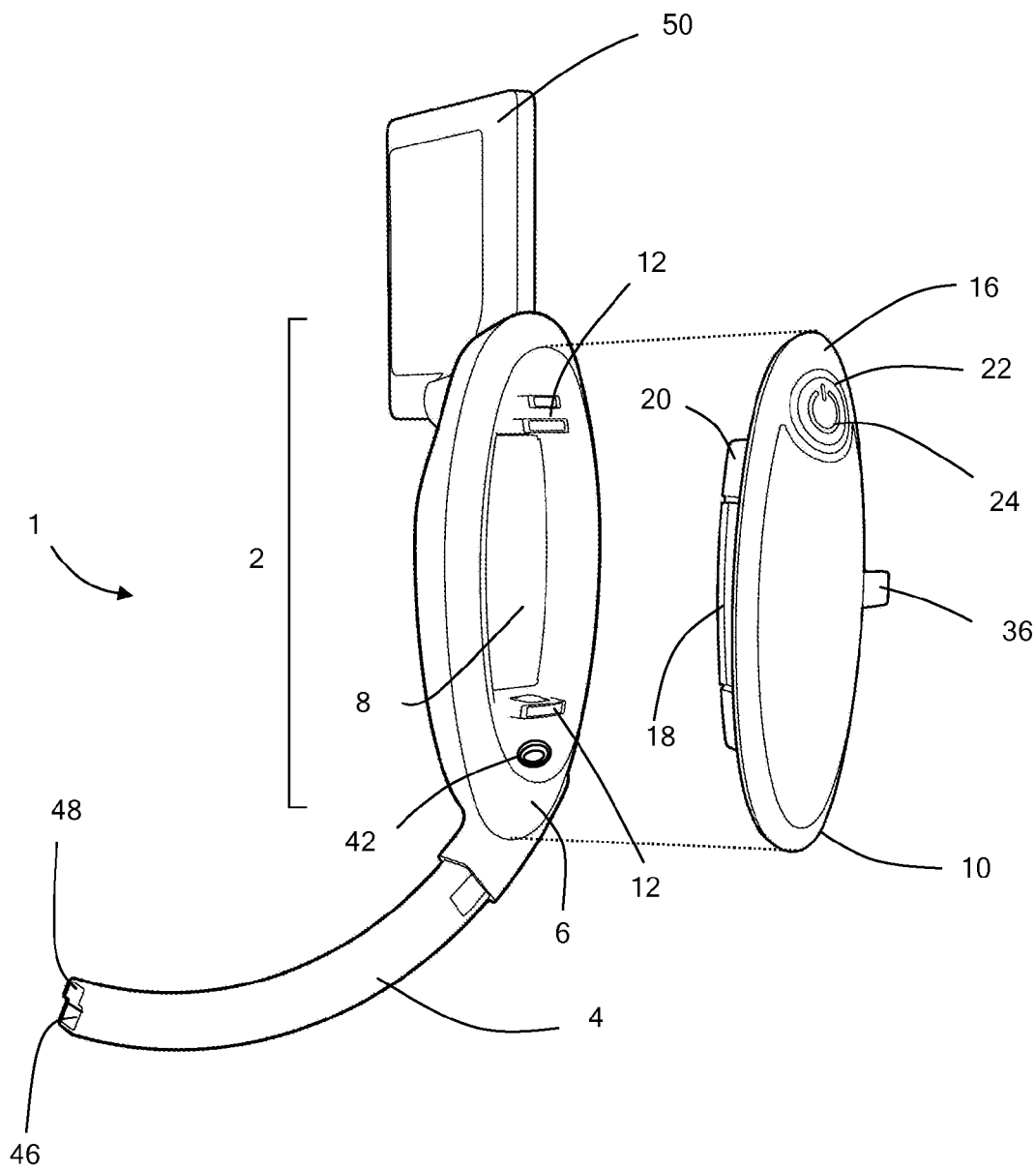
FIG. 2 is an exploded view of the video laryngoscope of FIG. 1 from an alternative angle.
Figure 3:
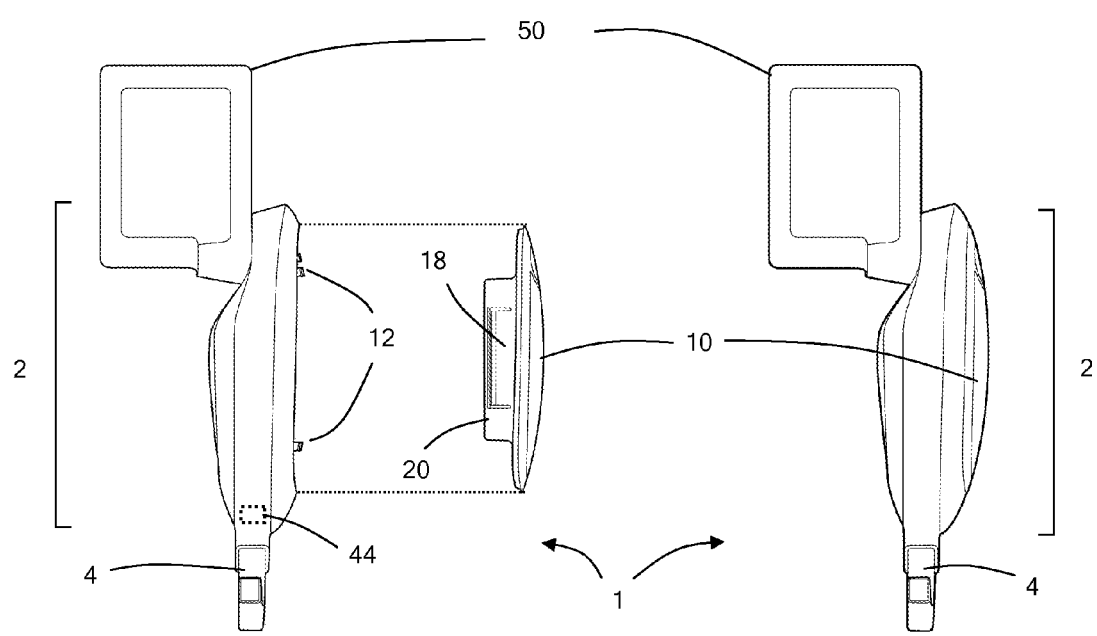
FIG. 3 is an exploded view from the front of the video laryngoscope of FIG. 1.
Figure 4:
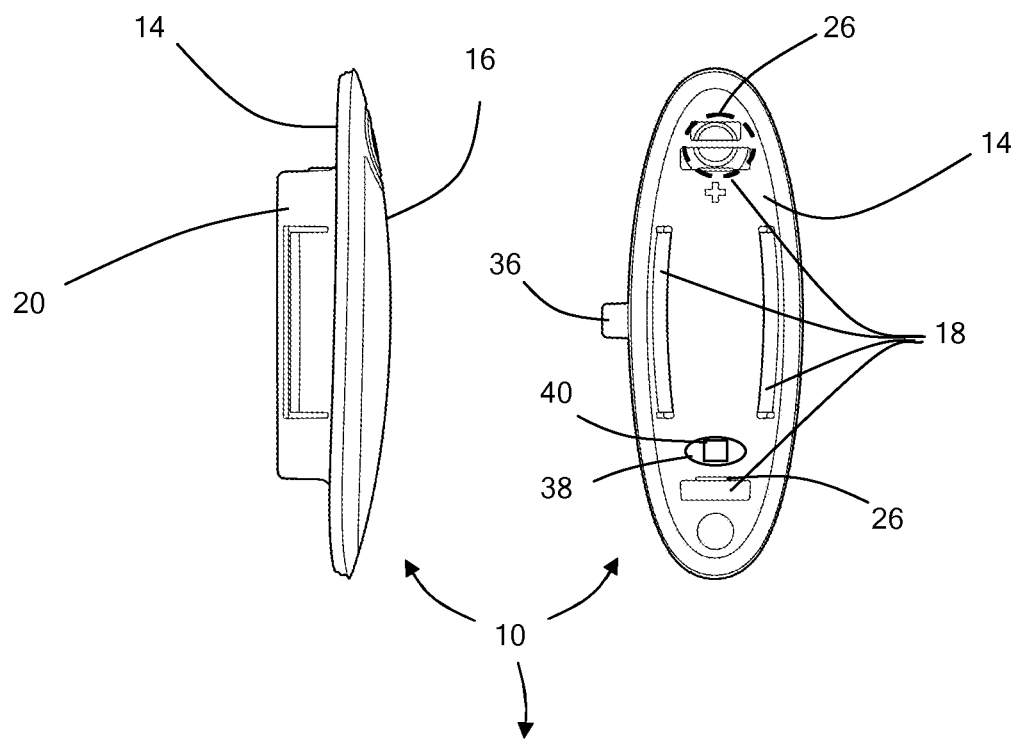
FIG. 4 shows side, base and front views of the demountable battery pack of FIG. 1.
Figure 4:
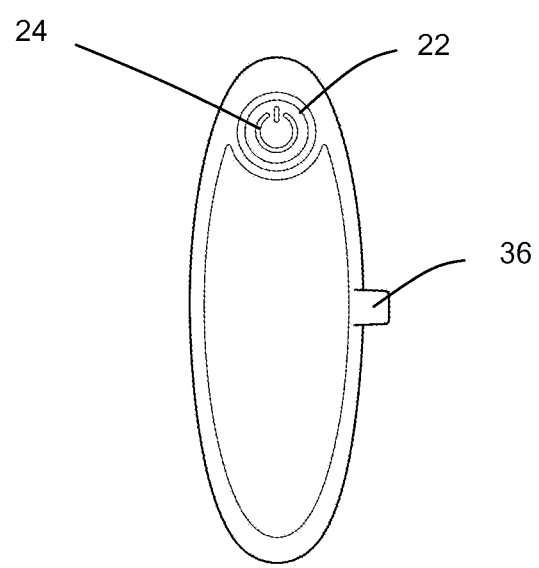
Figure 5A:
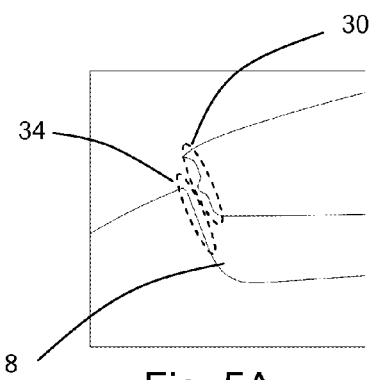
FIGS. 5A through 5D are sectional views through the electrical device before the battery pack is mounted (FIG. 5A), after the battery pack is mounted (FIG. 5B), with the battery pack and electrical device superimposed (FIG. 5C) and in expanded view (FIG. 5D)
Figure 5B:
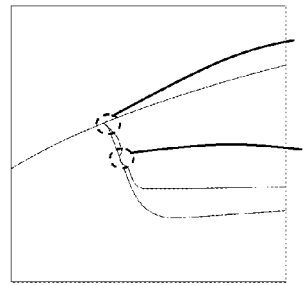
Figure 5C:
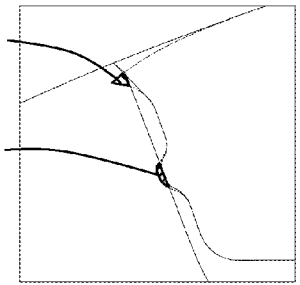
Figure 5D:
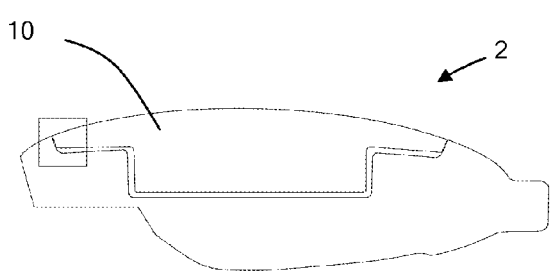
Figure 6:
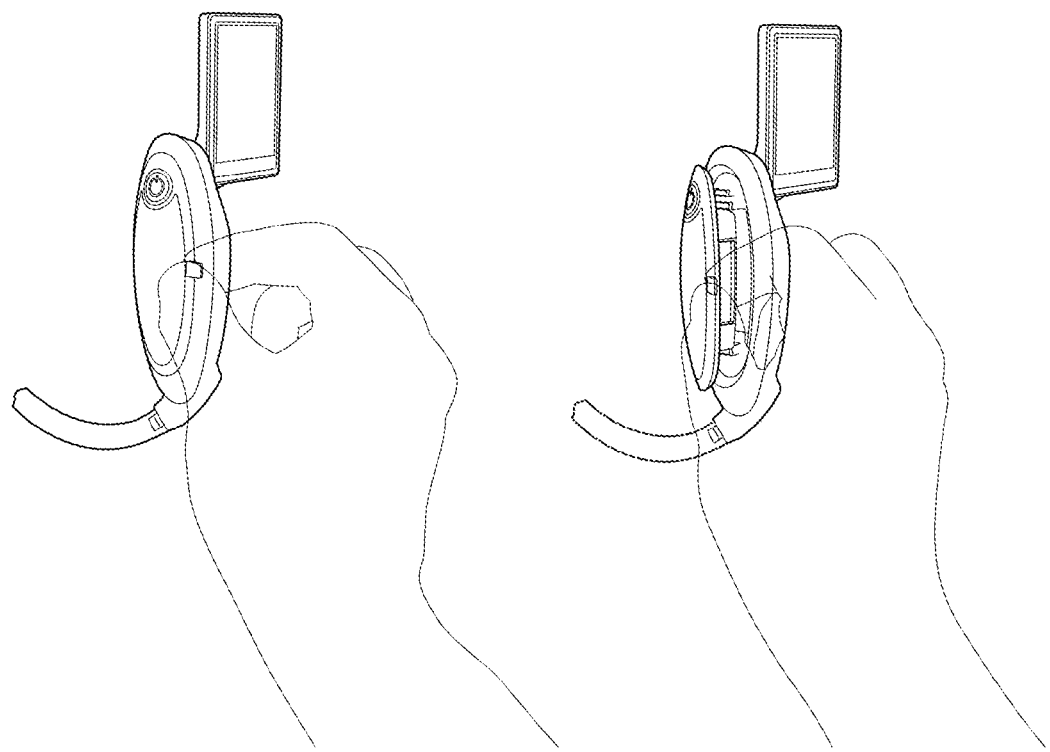
FIG. 6 is a perspective view of a laryngoscope having a battery pack with a tab, illustrating how a user may use the tab of the battery pack to remove the battery pack.
Figure 7:
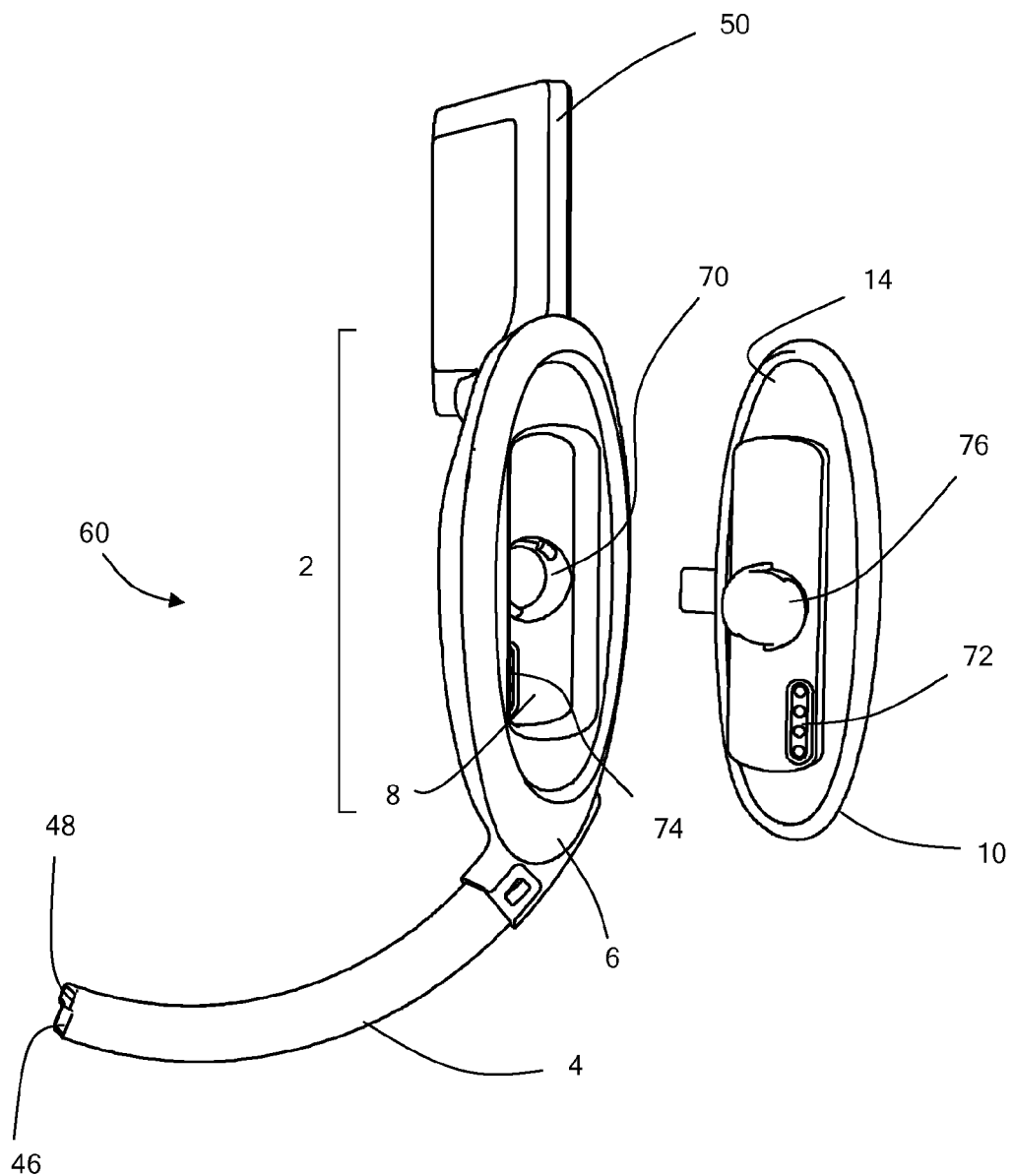
FIG. 7 is an exploded isometric view of a video laryngoscope with the battery pack removed.
Figure 8:
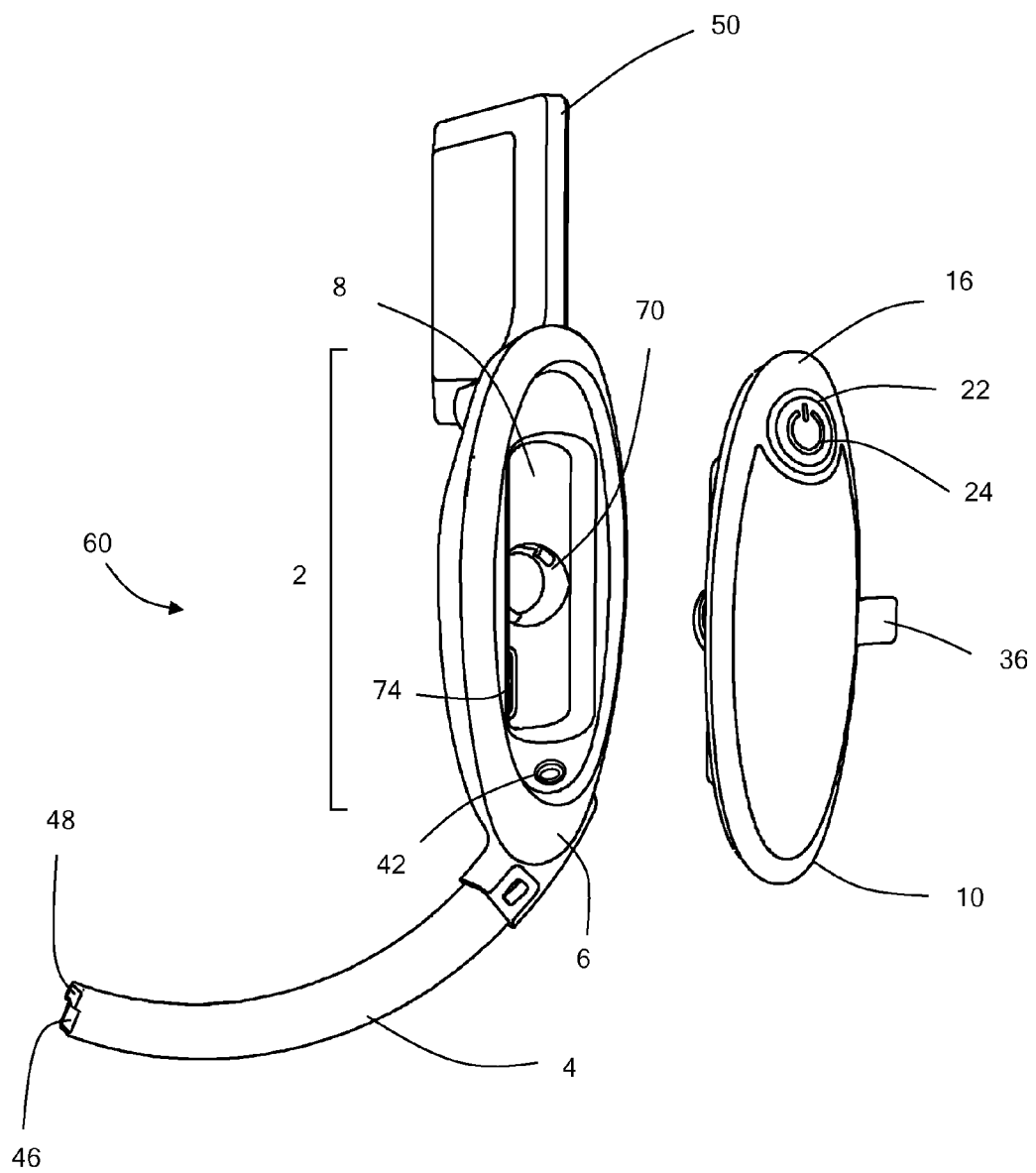
FIG. 8 is an exploded view of the video laryngoscope of FIG. 1 from an alternative angle.
Figure 9:
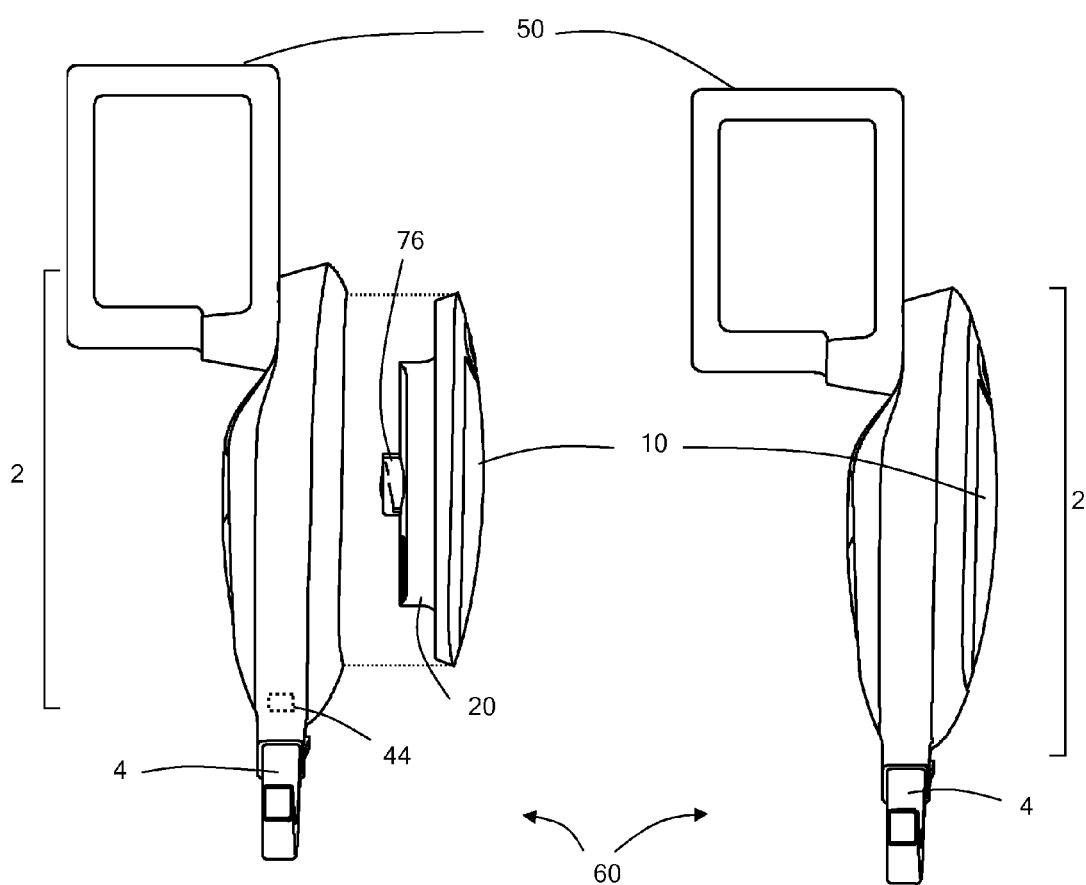
FIG. 9 is an exploded view from the front of the video laryngoscope of FIG. 8.
Figure 10:
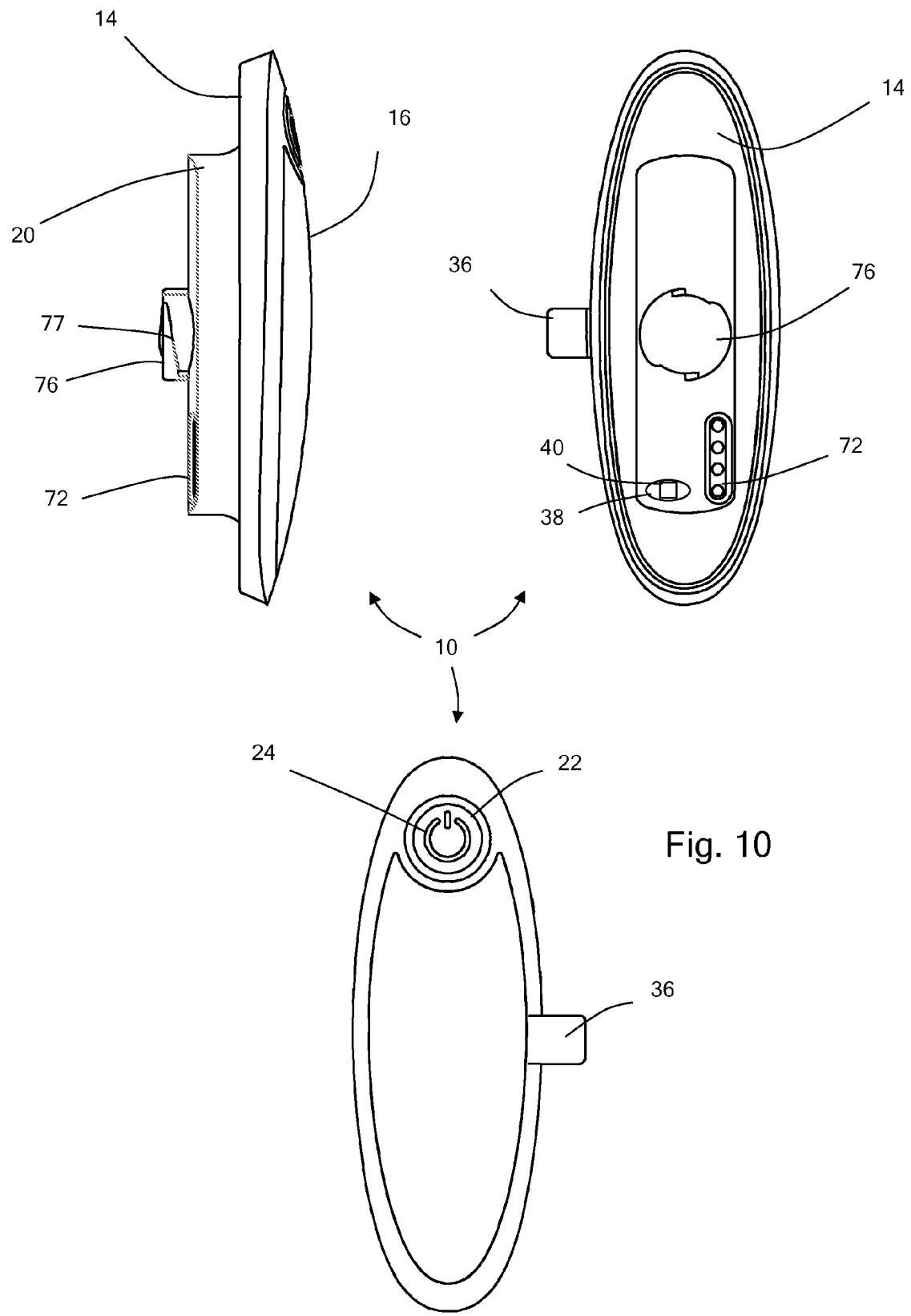
FIG. 10 shows side, base and front views of the demountable battery pack of FIG. 8.
Figure 11A:
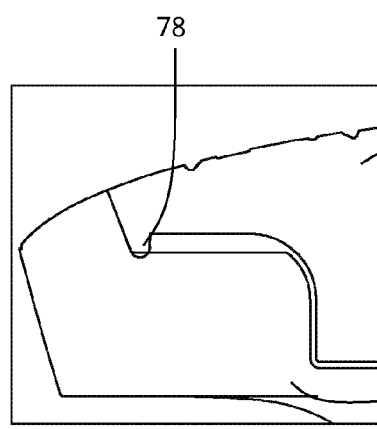
FIGS. 11A and 11B are sectional views through an embodiment of the electrical device where the seal is integral to the battery pack.
Figure 11C:
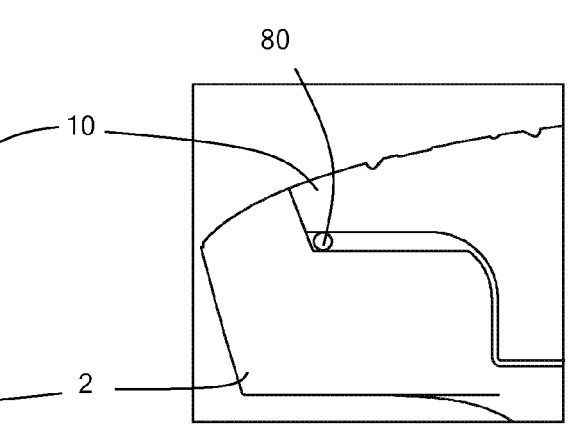
FIGS. 11C and 11D are sectional views through an alternative embodiment of the electrical device where the seal is a typical O-ring.
Figure 11B:
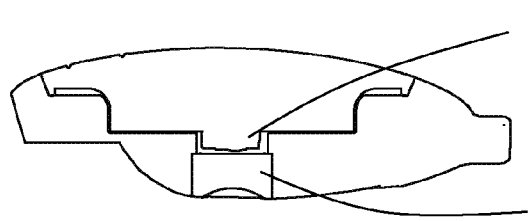
Figure 11D:
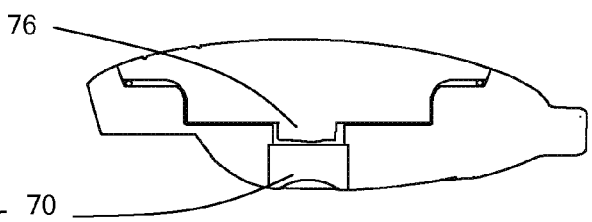

With reference to FIGS. 1 to 6 a video laryngoscope 1 (being an example of an electrical device) comprises a body 2, and an arm 4 extending from the body. When prepared for use, a disposable rigid plastic sheath (not shown) is demountably retained on the arm, functioning as a laryngoscope blade. The body portion comprises a first surface region 6, and a recess 8 for demountably receiving a battery pack 10.

The body comprises electrical contacts 12 (functioning as an input interface) for receiving electrical power from the battery pack, located within the recess. The battery pack comprises a first major surface 14 and a second, opposed major surface 16. The first major surface comprises battery retaining formations 18 which retain a battery 20 and, when the battery pack is installed on the body the first major surface faces the body. The second major surface comprises an activation switch 22 and a light emitting diode 24 which functions as a display informing the user whether the video laryngoscope is activated. When the battery pack is installed on the body, the second major surface becomes a part of the outer surface of the laryngoscope, forming a grip for a user, along with the first surface region 6. The battery pack comprises electrical contacts 26 (functioning as an output interface) through which power can be transmitted to the electrical contacts on the body of the electrical device when the battery pack is fitted and the device is switched on.

The battery pack comprises a first seal 28 on a coupling surface 30 extending around the perimeter of the battery pack and a second seal 32 also located on the coupling surface. The seals are each formed as flexible polymeric ridges. Upon installation of the battery pack onto the body, the seals are compressed between the coupling surface and a cooperating surface 34 of the electrical device forming a waterproof seal around the perimeter of the battery pack. Near the periphery of the battery pack a tab 36 stands proud of the second major surface, for use in removing the battery pack.

The battery pack includes an RFID tag 38 including memory 40, and the body includes a solenoid coil 42 operable to inductively power the RFID tag (when the battery pack is fitted to the device), to read data from the RFID tag memory and to write data to the memory.

The body of the laryngoscope includes a processor 44 which controls the functions of the laryngoscope, including a light 46, a video camera 48, a video display 50 for displaying images from the video camera, and the solenoid coil.

When a battery pack is attached (and so the device is in its assembled stated) a user begins operation of the device by pressing activation switch. The device powers up, switching on the video camera, video screen and light. The solenoid coil activates the RFID tag, reading the value stored in the memory. When the battery pack is new and unused, the value is a predetermined integer, such as 500. This value, or a number derived from it, is displayed on the screen as a numeral, or in another graphic format, such as a bar chart, pie chart, or any other graphical representation of available capacity.

As the device is used, the processor calculates the amount of usage. In some embodiments the processor simply determines the period of time for which the device is used. As the capacity of the battery pack is consumed, the value displayed on the screen is changed to reflect the reduced capacity, for example, the number 500 counts down. Periodically, the processor causes the solenoid coil to power up the RFID tag and write a new value to the memory of the RFID tag, reflecting the reduced available rated capacity of the battery pack. This may be carried out each time the stored value should change, or may be carried out once when the device is powered down. The value stored on the RFID tag can be updated quickly. As the activation switch is integral to the battery pack, a user cannot subvert the usage recording system by removing the battery pack to prevent the value stored on the RFID tag from being updated.

The processor may change the stored value depending solely on the amount of time for which the electrical device has been used, or used in one or more operating modes (e.g. modes in which the video screen is switched on in the case of a video laryngoscope). The processor may however take into account variations in power consumption by the device. More power will be consumed when a screen is on, for example, than when it is not. Thus, the processor may decrement the stored value more frequently in operating modes in which more power is consumed. The electrical device could include an ammeter but it is preferred to simply base changes to the value on measurements of the amount of time for which the device has been used, or used in specific operating modes, for simplicity. The processor may take into account environmental factors, such as temperature, measured by one or more sensors, such as a temperature sensor (e.g. a thermocouple), as such factors may affect battery life and/or power consumption.

Once the remaining available rated capacity of the battery pack reaches zero, or another threshold value as appropriate, the processor may cause the electronic device (or at least one function of the electronic device) to stop operating or to no longer start operating. The latter option may be preferable for a video laryngoscope used in an emergency environments as it could be dangerous for the device to stop functioning during an emergency procedure. It would be safer for it simply to not start functioning unless there was sufficient remaining available rated capacity to complete a procedure based on the known typical power consumption during that procedure. Before the device stops operating, or no longer starts operating, the device will typically output one or more audible or visual warnings.

As the stored value was initially chosen so that there was a high level of confidence that the capacity of the battery pack would not be exhausted before the remaining available rated capacity reached zero there will virtually always be some additional battery capacity available, although users should be discouraged from relying on or using this.

The device of the example embodiment also includes an override feature to enable a user to cause it to continue carrying out one or more functions, or to start carrying out one or more functions, even though the available rated capacity has dropped below the threshold. This may involve the user pressing a button but could involve another type of user interface. For example, the user may have to speak their name (which speech could be recorded), or to emit a loud noise at a loudspeaker of the device by shouting. Thus, an emergency override may be present but one which a user would not wish to use except in a genuine emergency.

Once the battery pack has been exhausted, it can be removed, breaking the seals. It is then replaced with a new battery pack which includes a new seal and so forms a good waterproof joint with the electrical device. The consumed battery pack is then disposed of, or preferably returned to the manufacturer for recycling or reconditioning.

The memory of the RFID tag may store additional data, such as an identifier of the battery pack, or of an electrical device to which it is or has been fitted. Some or all of the data stored on the RFID tag, such as the stored value described above, may be encoded to prevent tampering.

Although the invention has been illustrated with the example embodiment of a video laryngoscope, the invention may also be employed with other types of electrical devices.

Second Embodiment

All common features between the first and second embodiments are referred to by the same reference numerals.

With reference to FIGS. 7 to 12, a video laryngoscope 60 (being an example of an electrical device) comprises a body 2, and an arm 4 extending from the body. When prepared for use, a disposable rigid plastic sheath (not shown) is demountably retained on the arm, functioning as a laryngoscope blade. The body portion comprises a first surface region 6, and a recess 8 for demountably receiving a battery pack 10.

The battery pack comprises a first major surface 14 and a second, opposed major surface 16. The first major surface retains a battery 20 and, when the battery pack is installed on the body the first major surface faces the body. The second major surface comprises an activation switch 22 and a light emitting diode 24 which functions as a display informing the user whether the video laryngoscope is activated. When the battery pack is installed on the body, the second major surface becomes a part of the outer surface of the laryngoscope, forming a grip for a user, along with the first surface region 6. The battery pack comprises electrical contacts 72 (functioning as an output interface) through which power can be transmitted to the electrical contacts on the body of the electrical device 74 when the battery pack is fitted and the device is switched on. The battery pack comprises a cam bolt 76 having a camming surface 77.

The battery pack comprises a seal 78 on a coupling surface 30 extending around the perimeter of the battery pack. The seal is each formed as a flexible polymeric ridge. Upon installation of the battery pack onto the body, the seal is compressed between the coupling surface and a cooperating surface of the electrical device forming a waterproof seal around the perimeter of the battery pack. Near the periphery of the battery pack a tab 36 stands proud of the second major surface, for use in removing the battery pack.

In an alternative embodiment, battery pack does not comprise a seal and an "O-ring" 80 (acting as a seal) is provided between the battery pack and the surface of the recess.

The battery pack includes an RFID tag 38 including memory 40, and the body includes a solenoid coil 42 operable to inductively power the RFID tag (when the battery pack is fitted to the device), to read data from the RFID tag memory and to write data to the memory.

The body of the laryngoscope includes a processor 44 which controls the functions of the laryngoscope, including a light 46, a video camera 48, a video display 50 for displaying images from the video camera, and the solenoid coil.

The body of the laryngoscope further comprises a locking mechanism 70 extending from the recess to the surface of the body opposed to the recess. A portion of the locking mechanism extends into the recess and comprises a pair of teeth which may cooperatively interact with the cam bolt-type formation on the battery pack.

Figure 12:
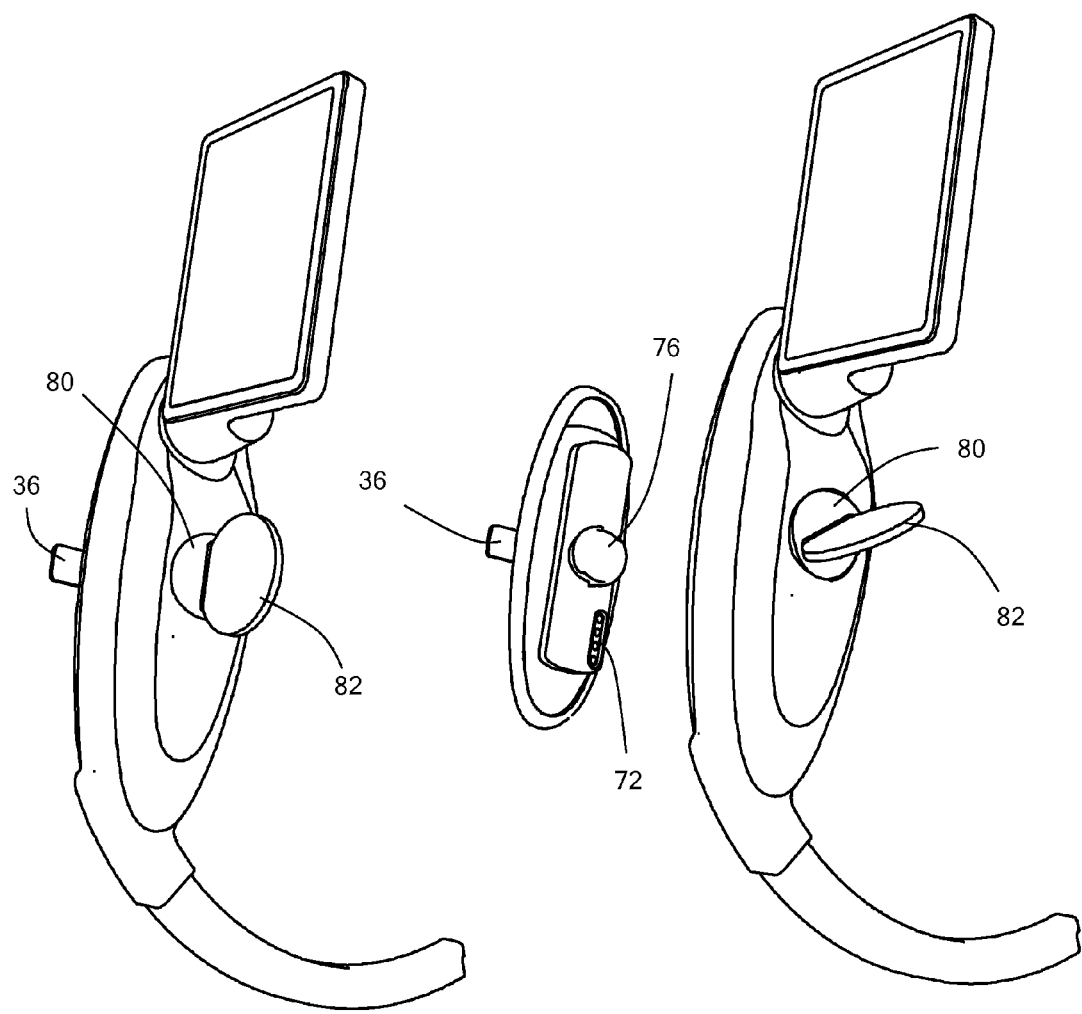
FIG. 12 shows a perspective view of the video laryngoscope illustrating the locking mechanism for fixing the battery pack tightly to the body.

As shown in FIG. 12, the locking mechanism comprises a slot on the surface of the body opposed to the recess. The slot may receive the edge of a coin such that turning the coin held within the slot turns the locking mechanism.

The battery pack is attached to the body by pressing the battery pack into the recess of the body such that the teeth of the locking mechanism interact with the camming surface of the cam bolt. A coin or similar is inserted into the slot and turned. The locking mechanism rotates within the body such that the teeth rotate around the camming surface, thereby urging the battery pack tightly against the body.

When a battery pack is attached (and so the device is in its assembled state) a user begins operation of the device by pressing activation switch. The device powers up, switching on the video camera, video screen and light. The solenoid coil activates the RFID tag, reading the value stored in the memory. When the battery pack is new and unused, the value is a predetermined integer, such as 500. This value, or a number derived from it, is displayed on the screen as a numeral, or in another graphic format, such as a bar chart, pie chart, or any other graphical representation of available capacity.

As the device is used, the processor calculates the amount of usage. In some embodiments the processor simply determines the period of time for which the device is used. As the capacity of the battery pack is consumed, the value displayed on the screen is changed to reflect the reduced capacity, for example, the number 500 counts down. Periodically, the processor causes the solenoid coil to power up the RFID tag and write a new value to the memory of the RFID tag, reflecting the reduced available rated capacity of the battery pack. This may be carried out each time the stored value should change, or may be carried out once when the device is powered down. The value stored on the RFID tag can be updated quickly. As the activation switch is integral to the battery pack, a user cannot subvert the usage recording system by removing the battery pack to prevent the value stored on the RFID tag from being updated.

The processor may change the stored value depending solely on the amount of time for which the electrical device has been used, or used in one or more operating modes (e.g. modes in which the video screen is switched on in the case of a video laryngoscope). The processor may however take into account variations in power consumption by the device. More power will be consumed when a screen is on, for example, than when it is not. Thus, the processor may decrement the stored value more frequently in operating modes in which more power is consumed. The electrical device could include an ammeter but it is preferred to simply base changes to the value on measurements of the amount of time for which the device has been used, or used in specific operating modes, for simplicity. The processor may take into account environmental factors, such as temperature, measured by one or more sensors, such as a temperature sensor (e.g. a thermocouple), as such factors may affect battery life and/or power consumption.

Once the remaining available rated capacity of the battery pack reaches zero, or another threshold value as appropriate, the processor may cause the electronic device (or at least one function of the electronic device) to stop operating or to no longer start operating. The latter option may be preferable for a video laryngoscope used in an emergency environments as it could be dangerous for the device to stop functioning during an emergency procedure. It would be safer for it simply to not start functioning unless there was sufficient remaining available rated capacity to complete a procedure based on the known typical power consumption during that procedure. Before the device stops operating, or no longer starts operating, the device will typically output one or more audible or visual warnings.

As the stored value was initially chosen so that there was a high level of confidence that the capacity of the battery pack would not be exhausted before the remaining available rated capacity reached zero there will virtually always be some additional battery capacity available, although users should be discouraged from relying on or using this.

The device of the example embodiment also includes an override feature to enable a user to cause it to continue carrying out one or more functions, or to start carrying out one or more functions, even though the available rated capacity has dropped below the threshold. This may involve the user pressing a button but could involve another type of user interface. For example, the user may have to speak their name (which speech could be recorded), or to emit a loud noise at a loudspeaker of the device by shouting. Thus, an emergency override may be present but one which a user would not wish to use except in a genuine emergency.

Once the battery pack has been exhausted, it can be removed, breaking the seals. It is then replaced with a new battery pack which includes a new seal and so forms a good waterproof joint with the electrical device. The consumed battery pack is then disposed of, or preferably returned to the manufacturer for recycling or reconditioning.

The memory of the RFID tag may store additional data, such as an identifier of the battery pack, or of an electrical device to which it is or has been fitted. Some or all of the data stored on the RFID tag, such as the stored value described above, may be encoded to prevent tampering.

Although the invention has been illustrated with the example embodiment of a video laryngoscope, the invention may also be employed with other types of electrical devices.

Further variation and modifications may be considered by one skilled in the art, within the scope of the invention herein disclosed.

The invention claimed is:

1. A video laryngoscope comprising a body and a battery pack demountably attachable to the body, the body of the video laryngoscope comprising at least one input interface for receiving power from a demountable battery pack, the demountable battery pack comprising a cover portion, a plurality of seals, a battery, and an output interface for transmitting electrical power, whereby the battery pack is demountably attachable to the body such that the input and output interfaces are in electrical communication, the cover portion of the battery pack forms part of the outer surface of the assembled device, and the seals form a waterproof seal between the demountable battery pack and the body of the video laryngoscope, the plurality of seals comprising a first seal and a second seal and the first and second seals are configured such that each forms a seal intermediate the outside of the medical device and the input and output interfaces, such the liquids outside the device would require to pass both seals in turn to penetrate the input and output interfaces.

2. A video laryngoscope according to claim 1, wherein the battery pack has a coupling surface extending around the battery pack, and the body of the video laryngoscope comprises a cooperating surface such that, when the battery pack is mounted to the body of the video laryngoscope, the coupling surface and cooperating surface fit against each other, with the first seal therebetween.

3. A video laryngoscope according to claim 1 wherein the first seal extends around the cover portion thereby forming a seal at the outer surface of the assembled device.

4. A video laryngoscope according to claim 1, wherein the body of the video laryngoscope comprises a recess for receiving the demountable battery pack and the cover portion occludes the recess when the device is assembled.

5. A video laryngoscope according to claim 1, wherein the first seal is compliant.

6. A video laryngoscope according to claim 1, wherein the first and second seals have different compositions, to resist different types of material.

7. A video laryngoscope according to claim 1, wherein the video laryngoscope comprises a handle and the cover of the battery pack forms a portion of the handle of the video laryngoscope.

8. A video laryngoscope according to claim 1, wherein the battery pack cover comprises an anti-slip surface to facilitate grip.

9. A video laryngoscope according to claim 1, wherein the battery pack comprises a switch operable to activate the video laryngoscope.

10. A video laryngoscope according to claim 1, wherein the battery pack comprises a release mechanism to detach the battery pack from the body of the video laryngoscope.

11. A video laryngoscope according to claim 1, wherein the laryngoscope comprises a handle and the cover of the battery pack forms part of the handle.

12. A kit comprising a demountable video laryngoscope battery pack of claim 1 and a video laryngoscope body comprising a handle and an arm, the demountable video laryngoscope battery pack and video laryngoscope body together forming a video laryngoscope.

13. A video laryngoscope comprising a body and a battery pack demountably attachable to the body, the body of the video laryngoscope comprising at least one input interface for receiving power from a demountable battery pack, the demountable battery pack comprising a cover portion, a seal, a battery, and an output interface for transmitting electrical power, whereby the battery pack is demountably attachable to the body such that the input and output interfaces are in electrical communication, the cover portion of the battery pack forms part of the outer surface of the assembled device, and the seal forms a waterproof seal between the demountable battery pack and the body of the video laryngoscope, wherein the cover portion of the battery pack comprises a locking formation operable to lock the battery pack tightly to the body of the electrical device, and wherein the body of the electrical device comprises a recess and a locking mechanism operable to cooperatively receive the locking formation of the battery pack, the locking mechanism allowing the user of the electrical device to apply force on to the seals of the battery pack and therefore form an effective seal between the cooperative surface of the electrical device body and the coupling surface of the battery pack.

14. A kit comprising a demountable video laryngoscope battery pack of claim 13 and a video laryngoscope body comprising a handle and an arm, the demountable video laryngoscope battery pack and video laryngoscope body together forming a video laryngoscope.

15. A video laryngoscope comprising a body and a battery pack demountably attachable to the body, the body of the video laryngoscope comprising at least one input interface for receiving power from a demountable battery pack, the demountable battery pack comprising a cover portion, a seal, a battery, and an output interface for transmitting electrical power, whereby the battery pack is demountably attachable to the body such that the input and output interfaces are in electrical communication, the cover portion of the battery pack forms part of the outer surface of the assembled device, and the seal forms a waterproof seal between the demountable battery pack and the body of the video laryngoscope, wherein the battery pack comprises an isolator to selectively isolate one terminal of the battery pack.

16. A kit comprising a demountable video laryngoscope battery pack of claim 15 and a video laryngoscope body comprising a handle and an arm, the demountable video laryngoscope battery pack and video laryngoscope body together forming a video laryngoscope.

17. A video laryngoscope comprising a body and a battery pack demountably attachable to the body, the body of the video laryngoscope comprising at least one input interface for receiving power from a demountable battery pack, the demountable battery pack comprising a cover portion, a seal, a battery, and an output interface for transmitting electrical power, whereby the battery pack is demountably attachable to the body such that the input and output interfaces are in electrical communication, the cover portion of the battery pack forms part of the outer surface of the assembled device, and the seal forms a waterproof seal between the demountable battery pack and the body of the video laryngoscope, wherein the battery pack comprises a memory storing a value indicative of the remaining available rated capacity of the one or more batteries and the video laryngoscope comprises a usage recording device operable to determine when the video laryngoscope is operated and to update the value stored in the memory responsive to such usage to reflect the consumption of power from the one or more batteries resulting from the said operation.

18. A kit comprising a demountable video laryngoscope battery pack of claim 17 and a video laryngoscope body comprising a handle and an arm, the demountable video laryngoscope battery pack and video laryngoscope together forming a video laryngoscope.

19. A demountable video laryngoscope battery pack comprising a cover portion, a seal, a battery, and an output interface for transmitting electrical power, whereby the battery pack is demountably attachable to a video laryngoscope body such that the input and output interfaces are in electrical communication, the cover portion of the battery pack forms part of the outer surface of the assembled video laryngoscope, which seal forms a seal between the demountable battery pack and the body of the video laryngoscope, further comprising a switch operable to activate a video laryngoscope, and an RFID tag.

20. A kit comprising a demountable video laryngoscope battery pack of claim 19 and a video laryngoscope body comprising a handle and an arm, the demountable video laryngoscope battery pack and video laryngoscope body together forming a video laryngoscope.

* * * * *